(12) United States Patent
Morita et al.

(10) Patent No.: US 8,946,297 B2
(45) Date of Patent: Feb. 3, 2015

(54) SOLID COMPOSITION FOR PEST CONTROL

(75) Inventors: Masayuki Morita, Osaka (JP); Takao Awazu, Kusatsu (JP); Akira Nakagawa, Kusatsu (JP); Taku Hamamoto, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 414 days.

(21) Appl. No.: 12/919,428

(22) PCT Filed: Mar. 18, 2009

(86) PCT No.: PCT/JP2009/055348
§ 371 (c)(1),
(2), (4) Date: Aug. 25, 2010

(87) PCT Pub. No.: WO2009/119420
PCT Pub. Date: Oct. 1, 2009

(65) Prior Publication Data
US 2011/0015237 A1    Jan. 20, 2011

(30) Foreign Application Priority Data
Mar. 24, 2008   (JP) ................................ 2008-075284

(51) Int. Cl.
*A61K 31/165* (2006.01)
*C07C 233/00* (2006.01)
*A01N 43/56* (2006.01)

(52) U.S. Cl.
CPC ..................................... *A01N 43/56* (2013.01)
USPC ........................................ 514/620; 564/164

(58) Field of Classification Search
USPC .......................................... 514/620; 564/164
See application file for complete search history.

(56) References Cited

U.S. PATENT DOCUMENTS

| | | |
|---|---|---|
| 6,458,745 B1 | 10/2002 | Runge et al. |
| 7,612,100 B2 | 11/2009 | Koyanagi et al. |
| 2010/0028304 A1 | 2/2010 | Koyanagi et al. |
| 2010/0035935 A1 | 2/2010 | Koyanagi et al. |

FOREIGN PATENT DOCUMENTS

| | | |
|---|---|---|
| WO | 03/039249 | 5/2003 |
| WO | WO 2005077934 A1 * | 8/2005 |
| WO | WO 2006/040113 A2 | 4/2006 |
| WO | WO 2007/081553 A2 | 7/2007 |
| WO | 2009/002856 | 12/2008 |

OTHER PUBLICATIONS

MacIsaac et al.; "A Scanning Electron Microscope Study of Glyphosate Deposits in Relation to Foliar Uptake"; 1991; Pestic. Sci.; 31:53-64.*
Koyanagi et al.; WO 2005/077934 A1; 2005; English machine translation obtained from Espacenet on Aug. 20, 2012.*
U.S. Appl. No. 13/003,895, filed Jan. 13, 2011, Hamamoto.
U.S. Appl. No. 13/867,854, filed Aug. 16, 2010, Morita, et al.
Egyptian Office Action issued Aug. 30, 2012, in Patent Application No. PCT 1581/2010 (with partial English-language translation).
Office Action issued Oct. 8, 2013, in JP Application No. 2009-053421.
Office Action issued Dec. 4, 2013, in EP Application No. 09723810 filed Mar. 18, 2009.
Thomas J. Monaco, et al., "Weed Science Principles and Practices", Fourth Edition (2002).
Office Action issued Oct. 8, 2013 in JP Patent Application No. 2009-053421.

\* cited by examiner

*Primary Examiner* — Paul Zarek
(74) *Attorney, Agent, or Firm* — Oblon, Spivak, McClelland, Maier & Neustadt, L.L.P.

(57) ABSTRACT

To provide an anthranilamide formulation compound for improving pest controlling effects.

A solid composition for pest control which comprises an amorphous anthranilamide compound or its salt as a pesticidal active ingredient, a nonionic surfactant and/or an anionic surfactant and a mineral carrier.

16 Claims, 1 Drawing Sheet

SOLID COMPOSITION FOR PEST CONTROL

TECHNICAL FIELD

The present invention relates to a solid composition for pest control comprising an anthranilamide compound of which the pesticidal activity is improved.

BACKGROUND ART

It has been known that anthranilamide type insecticides are useful for controlling pests such as Lepidoptera, and Patent Document 1 discloses as its formulations, various formulations such as an emulsifier, a wettable powder, a dust or granules. Further, Patent Document 2 discloses as a formulation which improves the effect of the compound for controlling pests, an oily suspension containing a hydrophobic solvent.
Patent Document 1: WO2005/077934
Patent Document 2: WO2007/081553

DISCLOSURE OF THE INVENTION

Problems to be Solved by the Invention

Many pesticides including anthranilamide type compounds have characteristic spectrums and effects respectively, but have some problems that the effects are sometimes inadequate to certain pests, that their residual activities are sometimes poor and the effects are not satisfactorily maintained for a certain period of time, and that adequate pesticidal effects cannot be practically achieved. Therefore, it has been desired to improve the controlling effects by a formulation method.

Means of Solving the Problems

The present inventors have conducted various studies to solve the above problems, and as a result found that the controlling effects against pests are remarkably improved by making an anthranilamide compound to be amorphous. Thus, the present invention has been accomplished.

That is, the present invention relates to a solid composition for pest control which is characterized by comprising an amorphous anthranilamide compound or a salt thereof as an active ingredient of a pesticide, a surfactant and a carrier. Further, the present invention relates to a wettable powder or water dispersible granules comprising the above components.

Effects of the Invention

The pesticidal composition of the present invention makes it possible to improve the effects of the anthranilamide compound and to control pests with a low dose of the compound.

BEST MODE FOR CARRYING OUT THE INVENTION

Figure 1:
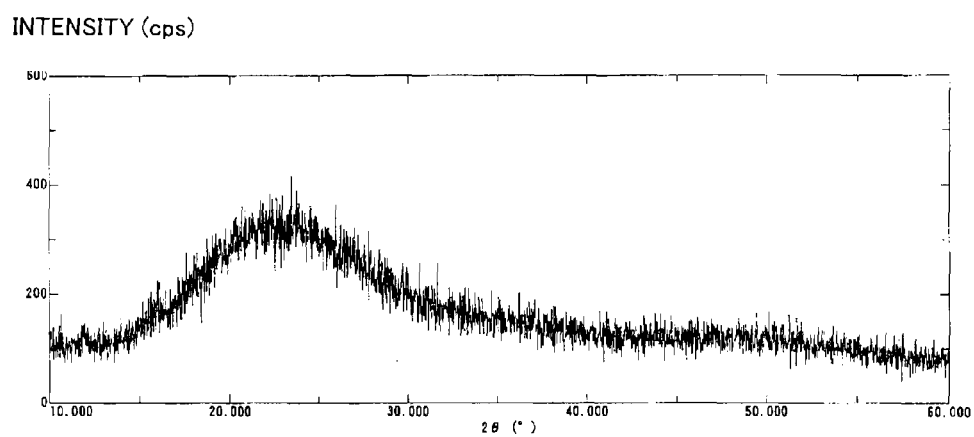
FIG. 1 is an X-ray powder diffraction image of Example 1.

The composition of the present invention comprises at least one amorphous anthranilamide compound or its salt, a surfactant and a carrier.

The anthranilamide compound or a salt thereof used in the present invention may, for example, be an anthranilamide compound represented by formula (I) or its salt:

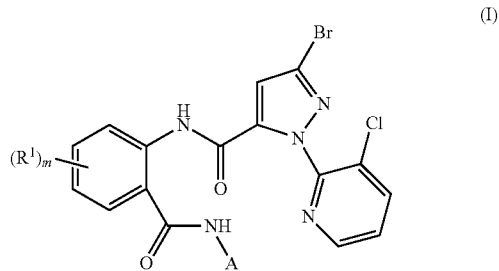

wherein $R^1$ is halogen, alkyl or cyano, A is alkyl which may be substituted by $C_{3-4}$ cycloalkyl, and m is from 0 to 4.

In the formula (I), the alkyl or the alkyl moiety of $R^1$ and A may be linear or branched. As a specific example, $C_{1-6}$ alkyl such as methyl, ethyl, propyl, isopropyl, butyl, pentyl or hexyl may be mentioned. Further, the halogen as $R^1$ may, for example, be each atom of fluorine, chlorine or bromine.

The salt of the anthranilamide compound includes all kinds of salts so long as they are agriculturally acceptable. Examples thereof include alkali metal salts such as a sodium salt and a potassium salt; alkaline earth metal salts such as a magnesium salt and a calcium salt; ammonium salts such as a dimethylammonium salt and a triethyl ammonium salt; inorganic acid salts such as a hydrochloride, a perchlorate, a sulfate and a nitrate; and organic acid salts such as an acetate and a methane sulfonate.

The anthranilamide compound is preferably the following compounds.
(1) 3-Bromo-N-(2-bromo-4-chloro-6-(1-cyclopropylethylcarbamoyl)phenyl)-1-(3-chloropyridin-2-yl)-1H-pyrazol-5-carboxamide (Compound 1)
(2) 3-Bromo-N-(4-chloro-2-(1-cyclopropylethylcarbamoyl)-6-methylphenyl)-1-(3-chloropyridin-2-yl)-1H-pyrazol-5-carboxamide (Compound 2)
(3) 3-Bromo-N-(2-bromo-4-chloro-6-(cyclopropylmethylcarbamoyl)phenyl)-1-(3-chloropyridin-2-yl)-1H-pyrazol-5-carboxamide (Compound 3)
(4) 3-Bromo-N-(4-chloro-2-methyl-6-(methylcarbamoyl)phenyl)-1-(3-chloropyridin-2-yl)-1H-pyrazol-5-carboxamide (Compound 4)
(5) 3-Bromo-1-(3-chloropyridin-2-yl)-N-(4-cyano-2-methyl-6-(methylcarbamoyl)phenyl)-1H-pyrazol-5-carboxamide (Compound 5)

The content of the anthranilamide compound or its salt in the composition is from 1 to 90 wt %, preferably from 5 to 80 wt %.

The anthranilamide compound or its salt has an average particle size of from 0.01 to 100 μm, preferably from 0.1 to 100 μm, and its crystal form is amorphous.

The crystal form of the compound is preferably complete amorphous, however, it may partially contain crystals.

The "amorphous" means a solid state having no regularity in alignment of atoms constituting a substance, and it is a solid state which shows a halo diffraction pattern, when measured by an X-ray powder diffraction apparatus. The amorphous has the same meaning as non-crystalline.

The amorphous substance can be prepared by drying treatment, mechanochemical treatment or solid dispersion treatment. As the drying treatment, spray drying or freeze drying may be mentioned. Further, the amorphous substance can be obtained also by heating and melting an original substance, followed by quenching. As the mechanochemical treatment, pulverization by means of a machine such as a grinding machine or mix pulverization with a polymer such as cellulose may be mentioned. An amorphous substance can be obtained also by dissolving an original substance together with a saccharide or a polymer in a solvent, followed by distilling off the solvent (solid dispersion treatment).

Further, in addition to the anthranilamide compound as an active ingredient, the composition of the present invention may contain other pesticides. Such other pesticides may, for example, be an insecticide, a miticide, a nematicide, a soil pesticide or a fungicide.

As the surfactant used in the present invention, one or more surfactants selected from the group consisting of a nonionic surfactant and an anionic surfactant may be used.

As the nonionic surfactant used in the present invention, the following surfactants may be mentioned.

Polyoxyalkylene surfactant: A polyoxyalkylene alkyl ether, a polyoxyethylene $C_{8-18}$ alkyl ether, a polyoxyethylene $C_{8-18}$ alkyl aryl ether, a polyoxyethylene $C_{8-18}$ alkyl phenyl ether, a polyoxyethylene (mono, di or tri)phenyl phenyl ether, a polyoxyethylene (mono, di or tri)benzyl phenyl ether, a polyoxypropylene (mono, di or tri)benzyl phenyl ether, a polyoxyethylene (mono, di or tri)styrylphenyl ether, a polyoxypropylene (mono, di or tri)styrylphenyl ether, a polymer of a polyoxyethylene (mono, di or tri)styrylphenyl ether, a polyoxyethylene polyoxypropylene block polymer, a $C_{8-18}$ alkyl polyoxyethylene polyoxypropylene block polymer ether, a $C_{8-12}$ alkyl phenylpolyoxyethylene polyoxypropylene block polymer ether, a polyoxyethylene bisphenyl ether, a polyoxyethylene resin acid ester, a polyoxyethylene $C_{8-18}$ aliphatic acid ester, a polyoxyethylene sorbitan $C_{8-18}$ aliphatic acid ester, a glycerol aliphatic acid ester ethylene oxide adduct, a castor oil ethylene oxide adduct, a cured castor oil ethylene oxide adduct, a $C_{8-18}$ alkylamine ethylene oxide adduct or a $C_{8-18}$ aliphatic acid amide ethylene oxide adduct may, for example, be mentioned.

Polyhydric alcohol surfactant: A glycerol aliphatic acid ester, a pentaerythritol aliphatic acid ester, a $C_{8-18}$ sorbitan aliphatic acid ester, a sucrose aliphatic acid ester, a polyhydric alcohol alkyl ether, an aliphatic acid alkanolamide, an alkyl glycoxide or an alkyl polyglycoside may, for example, be mentioned.

Among the above nonionic surfactants, preferred are the polyoxyethylene $C_{8-18}$ alkyl ether, the polyoxyethylene $C_{8-18}$ alkyl aryl ether, the polyoxyethylene $C_{8-18}$ alkyl phenyl ether, and the polyoxyethylene $C_{8-18}$ aliphatic acid ester.

As the anionic surfactant, the following surfactants may be mentioned.

Carboxylic acid surfactant: A polyacrylic acid, a polymethacrylic acid, a polymaleic acid, a polymaleic acid anhydride, a copolymer of an olefin (for example, isobutylene or diisobutylene) with maleic acid or maleic acid anhydride; a copolymer of acrylic acid with itaconic acid; a copolymer of methacrylic acid with itaconic acid; a copolymer of styrene with maleic acid or maleic acid anhydride; a copolymer of acrylic acid with methacrylic acid; a copolymer of acrylic acid with methyl acrylate; a copolymer of acrylic acid with a vinyl acetate; a copolymer of acrylic acid with maleic acid or maleic acid anhydride; a N-methyl $C_{12-18}$ aliphatic acid sarcocinate, a carboxylic acid such as a resin acid or a $C_{12-18}$ aliphatic acid; or a salt of such carboxylic acid may, for example, be mentioned.

Sulfuric acid ester surfactant: A $C_{12-18}$ alkyl sulfuric acid ester, a polyoxyethylene $C_{12-18}$ alkyl ether sulfuric acid ester, a polyoxyethylene alkyl aryl ether sulfuric acid ester, a polyoxyethylene aryl ether sulfuric acid ester, a polyoxyethylene $C_{8-12}$ alkyl phenyl ether sulfuric acid ester, a polyoxyethylene $C_{8-12}$ alkyl phenyl ether polymer sulfuric acid ester, a polyoxyethylene phenyl phenyl ether sulfuric acid ester, a polyoxyethylene benzylphenyl ether sulfuric acid ester, a polyoxyethylene styrylphenyl ether sulfuric acid ester, a polyoxyethylene styrylphenyl ether polymer sulfuric acid ester, a polyoxyethylene polyoxypropylene block polymer sulfuric acid ester, a sulfated oil, a sulfated aliphatic acid ester, a sulfuric acid ester such as sulfated aliphatic acid or sulfated olefin or a salt of such sulfuric acid ester may, for example, be mentioned.

Sulfonic acid surfactant: A $C_{12-22}$ alkyl sulfonic acid, a $C_{8-12}$ alkyl aryl sulfonic acid, a $C_{8-12}$ alkylbenzene sulfonic acid, a formaldehyde condensate of a $C_{8-12}$ alkylbenzene sulfonic acid, a formaldehyde condensate of cresol sulfonic acid, a $C_{14-16}$ α-olefin sulfonic acid, a $C_{8-12}$ alkyl sulfosuccinic acid, lignin sulfonic acid, a polyoxyethylene $C_{8-12}$ alkyl phenyl ether sulfonic acid, a polyoxyethylene aryl sulfonic acid, a polyoxyethylene $C_{12-18}$ alkyl ether sulfosuccinic acid half ester, a naphthalene sulfonic acid, a $C_{1-6}$ alkyl naphthalene sulfonic acid, a formaldehyde condensate of naphthalene sulfonic acid, a formaldehyde condensate of a $C_{1-6}$ alkyl naphthalene sulfonic acid, a formaldehyde condensate of creosote oil sulfonic acid, a $C_{8-12}$ alkyl diphenyl ether disulfonic acid, sulfonic acid such as a copolymer of methacrylic acid with a polystyrene sulfonic acid and styrene sulfonic acid, or a salt of such sulfonic acid may, for example, be mentioned.

Phosphoric acid ester surfactant: A $C_{8-12}$ alkyl phosphoric acid ester, a polyoxyethylene $C_{12-18}$ alkyl ether phosphoric acid ester, a polyoxyethylene $C_{8-12}$ alkyl phenyl ether phosphoric acid ester, a polyoxyethylene $C_{8-12}$ alkyl phenyl ether polymer phosphoric acid ester, a polyoxyethylene phenyl phenyl ether phosphoric acid ester, a polyoxyethylene benzyl phenyl ether phosphoric acid ester, a polyoxyethylene styrylphenyl ether phosphoric acid ester, a polyoxyethylene styrylphenyl ether polymer phosphoric acid ester, a polyoxyethylene polyoxypropylene block polymer phosphoric acid ester, a phosphatidylcholine, a phosphatidylethanolimine or a phosphoric acid condensate (such as tripolyphosphoric acid) or a salt of such phosphoric acid ester may, for example, be mentioned.

The salt of the anionic surfactant may, for example, be an alkali metal (such as lithium, sodium or potassium), an alkaline earth metal (such as calcium or magnesium), ammonium or each amine (such as alkylamine, cycloalkylamine or alkanolamine).

Among the above anionic surfactants, preferred are the polyoxyethylene alkyl aryl ether sulfuric acid ester salt, the polyoxyethylene aryl ether sulfuric acid ester salt, the $C_{12-22}$ alkyl sulfonate salt, the $C_{8-12}$ alkylbenzene sulfonate salt, the $C_{8-12}$ alkyl sulfosuccinate salt, the lignin sulfonate salt, the polyoxyethylene aryl sulfonate salt and the formalin condensate of naphthalene sulfonate salt.

The surfactant is preferably at least one selected from the group consisting of a polyoxyethylene $C_{8-18}$ alkyl ether, a polyoxyethylene $C_{8-18}$ alkyl aryl ether, a polyoxyethylene $C_{8-18}$ alkyl phenyl ether, a polyoxyethylene $C_{8-18}$ aliphatic acid ester, a polyoxyethylene alkyl aryl ether sulfuric acid ester salt, a polyoxyethylene aryl ether sulfuric acid ester salt, a $C_{12-22}$ alkyl sulfonate salt, a $C_{8-12}$ alkyl benzene sulfonate salt, a $C_{8-12}$ alkyl sulfosuccinate salt, a lignin sulfonate salt, a polyoxyethylene aryl sulfonate and a formalin condensate of naphthalenesulfonate salt.

The content of the surfactant in the composition is from 0.5 to 40 wt %, preferably from 1 to 20 wt %.

The carrier which can be used in the present invention may, for example, be a mineral carrier, a plant carrier or a polymer carrier.

The mineral carrier may, for example, be a kaoline such as kaolinite, dickite, nacrite or halloysite; a serpentine such as chrysotile, lizardite, antigorite or amesite; a montmorillonite such as sodium montmorillonite, calcium montmorillonite or magnesium montmorillonite; a smectite such as saponite, hectorite, sauconite or beidellite; a mica such as pyrophyllite, talc, agalmatolite, muscovite, phengite, sericite or illite; a silica such as cristobalite or quartz; a hydromagnesium silicate such as bentonite, attapulgite or sepiolite; a calcium carbonate such as dolomite or calcium carbonate fine powder; a sulfuric acid mineral such as gypsum or calcium sulfate; zeolite; boiling stone; volcanic tuff; vermiculite; laponite; pumice; diatomaceous earth; acid clay; activated clay; clay; a synthetic carrier such as white carbon or titanium dioxide.

The plant carrier may, for example, be cellulose, hull, flour, wood flour, starch, a rice bran, a wheat bran or soybean powder.

The polymer carrier may, for example, be methyl cellulose, Arabia gum, hydroxypropyl cellulose, hydroxypropyl methyl cellulose, dextran, sodium alginate, carboxymethyl cellulose sodium, propylene glycol alginic acid ester, polyvinyl pyrrolidone, polyvinyl alcohol, carboxyvinyl polymer, gazein sodium or dexitrin. As other carriers, urea, lactose, ammonium sulfate, sucrose, sodium chloride, sodium sulfate, sodium carbonate, potassium carbonate, potassium pyrophosphate, sodium tripolyphosphate, maleic acid, fumaric acid, citric acid and malic acid may, for example, be mentioned.

Among the above carriers, preferred is the mineral carrier, and the mineral carrier is preferably at least one selected from the group consisting of kaolin, talc, calcium carbonate, diatomaceous earth, clay and white carbon.

The content of the carrier based on the wettable powder of the present invention is usually from 3 to 95 wt %, preferably from 10 to 90 wt %.

The formulation of the composition of the present invention may, for example, be a powder, a driftless dust, granules, microgranules, microcapsules formulation, a wettable powder or water dispersible granules. The formulation is preferably the wettable powder or the water dispersible granules.

The above composition can be prepared by combining one or plural components selected from the group consisting of disingrators, stabilizers, pH controlling agents, dyes and odor masking agents, in addition to the amorphous anthranilamide compound or its salt, the surfactant and the carrier.

Now, methods for producing preferred formulations of the composition of the present invention will be described.

(1) Wettable Powder

The wettable powder of the present invention is a powder composition comprising an amorphous anthranilamide compound or its salt, a surfactant and a carrier and usually can be prepared by mixing the above components by a mixer such as a V-shaped mixer. The wettable powder thus prepared usually has an average particle size of at most 50 µm.

(2) Water Dispersible Granules

The water dispersible granules of the present invention are a solid granular composition comprising an amorphous anthranilamide compound or its salt, a surfactant and a carrier.

Such water dispersible granules can be prepared by a granulation method which is commonly used for preparing formulations of agricultural chemicals. The granulation method may, for example, be an extrusion granulation method, an impregnation granulation method, a compression granulation method, a stirring granulation method, a fluidized granulation method, a rolling granulation method or a spray granulation method.

One example of the method for preparing water dispersible granules by the extrusion granulation method will be described below.

An amorphous anthranilamide compound or its salt, a surfactant and a carrier are mixed, and then usually from 0.1 to 100 wt % of water is dropwise added or sprayed to the mixture, followed by kneading to prepare a kneaded mixture. Then, the kneaded mixture is granulated by a granulation machine, dried, sized and sieved to obtain water dispersible granules.

The granulation machine used in the granulation may, for example, be a basket type extrusion granulation machine or a dome type extrusion granulation machine, and the drying machine may, for example, be a fluidized drying machine or a bed type drying machine. The sizing machine may, for example, be Marumerizer, a pin mill or a shredder, and the sieving machine may, for example, be Gyro•Shifters or an electromagnetic vibration type sieving machine. The water dispersible granules thus produced have an average particle size of usually from about 0.3 to 10 mm, preferably from about 0.3 to 5 mm.

The composition of the present invention is preferably the following composition.

(1) A composition which comprises an amorphous anthranilamide compound or its salt, a nonionic surfactant and/or an anionic surfactant and a mineral carrier.

(2) A composition which comprises an amorphous anthranilamide compound or its salt, at least one surfactant selected from the group consisting of a polyoxyethylene $C_{8-18}$ alkyl ether, a polyoxyethylene $C_{8-18}$ alkyl aryl ether, a polyoxyethylene $C_{8-18}$ alkyl phenyl ether, a polyoxyethylene $C_{8-18}$ aliphatic acid ester, a polyoxyethylene alkyl aryl ether sulfuric acid ester salt, a polyoxyethylene aryl ether sulfuric acid ester salt, a $C_{12-22}$ alkyl sulfonate salt, a $C_{8-12}$ alkyl benzene sulfonate salt, a $C_{8-12}$ alkyl sulfosuccinate salt, a lignin sulfonate salt, a polyoxyethylene aryl sulfonate salt and a formalin condensate of naphthalenesulfonate salt; and at least one carrier selected from the group consisting of kaolin, talc, calcium carbonate, diatomaceous earth, clay and white carbon.

(3) The composition according to the above (1) or (2), which comprises from 1 to 90 wt % of the amorphous anthranilamide compound or its salt, from 0.5 to 40 wt % of the surfactant and from 3 to 95 wt % of the carrier.

(4) The composition according to the above (3), which comprises the amorphous anthranilamide compound or its salt, the polyoxyethylene $C_{8-18}$ alkyl ether, the polyoxyethylene $C_{8-18}$ alkyl phenyl ether, the polyoxyethylene alkyl aryl ether sulfuric acid ester salt, the alkyl benzene sulfonate salt, the clay and the white carbon.

The composition of the present invention is usually diluted with water and used for spray treatments. Although the dilution ratio varies depending on the content of the active ingredient in the composition, sites to be applied, etc., the composition is usually diluted from 5 to 100,000 times, preferably from 10 to 100,000 times, more preferably from 50 to 10,000 times.

EXAMPLES

Now, the present invention will be described in detail with reference to Examples and Test Examples, but it should be understood that the present invention is by no means restricted thereto.

Further, the following carriers and surfactants were used in Examples.

Carplex CS-7: white carbon (manufactured by Evonik Degussa Japan)

Sorpol 5073: polyoxyethylene alkyl aryl ether sulfuric acid ester.ammonium salt and polyoxyethylene alkyl ether (manufactured by Toho Chemical Industry Co., Ltd.)

Sorpol 5060: alkylbenzene sulfonic acid sodium salt (manufactured by Toho Chemical Industry Co., Ltd.)

Noigen EA-33: polyoxyethylene dodecyl phenyl ether (manufactured by Dai-ichi Kogyo Seiyaku Co., Ltd.)

Example 1

5 wt % of Carplex CS-7 was mixed with the compound (1), and the mixture was mortar pulverized by using an Ishikawa-type stirring grinding machine (manufactured by Ishikawa Kojo: AGA type) for 15 minutes. 2.2 g of the obtained pulverized product (average particle size: 9.2 μm) was mixed with 1.2 g of Sorpol 5073, 0.8 g of Sorpol 5060, 0.4 g of Noigen EA-33, 6 g of Carplex CS-7 and 29.4 g of clay, followed by mix-pulverization by a centrifugal pulverizing machine (manufactured by NIHONSEIKI KAISHA LTD.: φ screen: 1 mm, 10,000 rpm) to obtain a wettable powder containing 5 wt % of the compound (1).

The pulverized product obtained by the mortar pulverization had an average particle size of 9.2 μm, and as a result of the X-ray powder diffraction measurement, the crystal form was amorphous. FIG. 1 shows the result of the X-ray powder diffraction. The X-ray powder diffraction measurement was carried out by using RINT 1200 (Cu-Kα1) (manufactured by Rigaku Corporation).

Example 2

0.53 g of the compound (1) was mixed with 0.3 g of Sorpol 5073, 0.2 g of Sorpol 5060, 0.1 g of Noigen EA-33, 1.5 g of Carplex CS-7 and 7.4 g of clay, and then the mixture was mortar pulverized by using an Ishikawa-type stirring grinding machine for 15 minutes to obtain a wettable powder containing 5 wt % of the compound (1).

Further, the grinded product obtained by the mortar pulverization was subjected to X-ray powder diffraction measurement, and as a result only peaks derived from the clay were observed, and a peak derived from the compound (1) was not observed.

Comparative Example 1

The crystal compound (1) was pulverized by using a Turbo Counter Jet Mill (TJ-60, manufactured by TURBO KOGYO CO., LTD.). Then, 2.1 g of fine particles of the obtained compound (1) (average particle size: 2μ) was mixed with 1.2 g of Sorpol 5073, 0.8 g of Sorpol 5060, 0.4 g of Noigen EA-33, 6 g of Carplex CS-7 and 29.5 g of clay, and then the mixture was mix-pulverized by a centrifugal pulverizing machine (manufactured by NIHONSEIKI KAISHA LTD.: diameter of 1 mm screen, 10,000 rpm) to obtain a wettable powder containing 5% of the compound (1).

Figure 2:
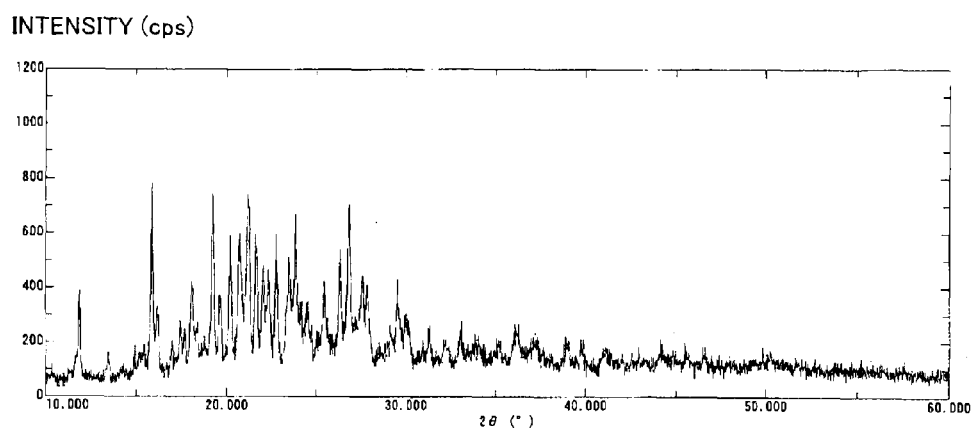
FIG. 2 is an X-ray powder diffraction image of Comparative Example 1.

Further, the product pulverized by a turbo counter jet mill was subjected to X-ray powder diffraction measurement, and as a result it was crystalline. FIG. 2 shows the result of the X-ray powder diffraction.

Test Example 1

Efficacy Against Silverleaf Whitefly (1) Preparation of Sample Solutions

Compositions obtained in Examples 1 and 2 and Comparative Example 1 (active ingredient: 5 wt %) were diluted 4,000 times with water respectively to prepare 12.5 ppm test liquids.

(2) Efficacy Test

Adults of silverleaf whitefly were released on cucumber with only one first true leaf left and other leaves cut off and planted in a pot, and permitted to lay eggs for about 24 hours. Thereafter, the pot was left for 9 days in a constant temperature chamber at 25° C. with lightening. The number of first instar nymphs was counted, and then, the test liquid of 12.5 ppm was sprayed uniformly on the leaf by a hand spray. After the treatment, the pot was left in a constant temperature chamber at 25° C. with lightening for 10 days, whereupon the number of old instar nymphs and the number of pupae were counted, and the controlling value was obtained by the following equation. Table 1 shows the test results. From Table 1, it is evident that the controlling effect of the formulation of the present invention is superior to that of Comparative Example.

Controlling value (%)=$(1-((Ta \times Cb)/(Tb \times Ca))) \times 100$

Ta: The number of old instar nymphs+the number of pupae after the treatment at the treated section Tb: The number of first instar nymphs before the treatment at the treated section Ca: The number of old instar nymphs+the number of pupae after the treatment at untreated section Cb: the number of first instar nymphs before the treatment at the untreated section

TABLE 1

|  | Controlling value (%) |
|---|---|
| Not treated | 0 |
| Ex. 1 | 97 |
| Ex. 2 | 95 |
| Comp. Ex. 1 | 55 |

INDUSTRIAL APPLICABILITY

The agricultural chemical composition containing the anthranilamide compound of the present invention is useful for controlling pests.

The entire disclosure of Japanese Patent Application No. 2008-075284 filed on Mar. 24, 2008 including specification, claims, drawings and summary is incorporated herein by reference in its entirety.

The invention claimed is:

1. A solid composition comprising an amorphous anthranilamide compound or its salt, a surfactant and a carrier.

2. The composition according to claim 1, wherein the anthranilamide compound is at least one compound selected from the group consisting of 3-bromo-N-(2-bromo-4-chloro-6-(1-cyclopropylethylcarbamoyl)phenyl)-1-(3-chloropyridin-2-yl)-1H-pyrazol-5-carboxamide, 3-bromo-N-(4-chloro-2-(1-cyclopropylethylcarbamoyl)-6-methylphenyl)-1-(3-chloropyridin-2-yl)-1H-pyrazol-5-carboxamide, 3-bromo-N-(2-bromo-4-chloro-6-(cyclopropylmethylcarbamoyl)phenyl)-1-(3-chloropyridin-2-yl)-1H-pyrazol-5-carboxamide, 3-bromo-N-(4-chloro-2-methyl-6-(methylcarbamoyl)phenyl)-1-(3-chloropyridin-2-yl)-1H-pyrazol-5- carboxamide and 3-bromo-1-(3-chloropyridin-2-yl)-N-(4-cyano-2-methyl-6-(methylcarbamoyl)phenyl)-1H-pyrazol-5-carboxamide.

3. The composition according to claim 1, wherein the surfactant is a nonionic surfactant and/or an anionic surfactant.

4. The composition according to claim 1, wherein the surfactant is at least one selected from the group consisting of a polyoxyethylene $C_{8-18}$ alkyl ether, a polyoxyethylene $C_{8-18}$ alkyl aryl ether, a polyoxyethylene $C_{8-18}$ alkyl phenyl ether, a polyoxyethylene $C_{8-18}$ aliphatic acid ester, a polyoxyethylene alkyl aryl ether sulfuric acid ester salt, a polyoxyethylene aryl ether sulfuric acid ester salt, a $C_{12-22}$ alkyl sulfonate salt, a $C_{8-12}$ alkyl benzene sulfonate salt, a $C_{8-12}$ alkyl sulfosuccinate salt, a lignin sulfonate salt, a polyoxyethylene aryl sulfonate salt and a formalin condensate of naphthalenesulfonate salt.

5. The composition according to claim 1, wherein the carrier is a mineral carrier.

6. The composition according to claim 1, wherein the carrier is at least one selected from the group consisting of kaolin, talc, calcium carbonate, diatomaceous earth, clay and white carbon.

7. The composition according to claim 1, which comprises the amorphous anthranilamide compound or its salt, a nonionic surfactant and/or an anionic surfactant and a mineral carrier.

8. The composition according to claim 1, which comprises the amorphous anthranilamide compound or its salt, at least one surfactant selected from the group consisting of a polyoxyethylene $C_{8-18}$ alkyl ether, a polyoxyethylene $C_{8-18}$ alkyl aryl ether, a polyoxyethylene $C_{8-18}$ alkyl phenyl ether, a polyoxyethylene $C_{8-18}$ aliphatic acid ester, a polyoxyethylene alkyl aryl ether sulfuric acid ester salt, a polyoxyethylene aryl ether sulfuric acid ester salt, a $C_{12-22}$ alkyl sulfonate salt, a $C_{8-12}$ alkyl benzene sulfonate salt, a $C_{8-12}$ alkyl sulfosuccinate salt, a lignin sulfonate salt, a polyoxyethylene aryl sulfonate salt and a formalin condensate of naphthalenesulfonate salt; and at least one carrier selected from the group consisting of kaolin, talc, calcium carbonate, diatomaceous earth, clay and white carbon.

9. The composition according to claim 1, which is a wettable powder or water dispersible granules.

10. A process of controlling pests, comprising applying the composition of claim 1 to a surface.

11. The composition according to claim 1, wherein the anthranilamide compound is contained in an amount of from 1 to 90 wt % based on the weight of the composition.

12. The composition according to claim 1, wherein the anthranilamide compound is contained in an amount of from 5 to 80 wt % based on the weight of the composition.

13. The composition according to claim 1, wherein the average particle size of the anthranilamide compound is from 0.01 to 100 μm.

14. The composition according to claim 1, wherein the average particle size of the anthranilamide compound is from 0.1 to 100 μm.

15. The composition according to claim 1, wherein the anthranilamide compound is 3-bromo-N-(2-bromo-4-chloro-6-(1-cyclopropylethylcarbamoyl)phenyl)-1-(3-chloropyridin-2-yl)-1H-pyrazol-5-carboxamide, and the composition comprises from 0.5 to 40 wt % of surfactant, based on the total weight of the composition.

16. The composition according to claim 1, wherein the anthranilamide compound is 3-bromo-N-(2-bromo-4-chloro-6-(1-cyclopropylethylcarbamoyl)phenyl)-1-(3-chloropyridin-2-yl)-1H-pyrazol-5-carboxamide, and the composition comprises from 1 to 20 wt % of surfactant, based on the total weight of the composition.

* * * * *